United States Patent [19]

Wisotzki et al.

[11] Patent Number: 4,900,545
[45] Date of Patent: Feb. 13, 1990

[54] HAIR SPLIT-END REGENERATION COMPOSITION

[75] Inventors: Klaus-Dieter Wisotzki, Erkrath; Horst Hoeffkes, Duesseldorf; Detlef Hollenberg, Hilden, all of Fed. Rep. of Germany

[73] Assignee: Henkel Kommanditgesellschaft auf Aktien, Duesseldorf, Fed. Rep. of Germany

[21] Appl. No.: 177,748

[22] Filed: Apr. 6, 1988

[30] Foreign Application Priority Data

Apr. 8, 1987 [DE] Fed. Rep. of Germany ....... 3711841

[51] Int. Cl.⁴ .................... A61K 7/075; A61K 31/70; A61K 7/08
[52] U.S. Cl. ..................................... 424/70; 514/772; 514/777
[58] Field of Search ................... 424/70; 514/772, 777

[56] References Cited

U.S. PATENT DOCUMENTS

| | | | |
|---|---|---|---|
| 4,070,452 | 1/1978 | Borchorst | 424/70 |
| 4,656,043 | 4/1987 | Hawkins et al. | 424/70 |
| 4,666,712 | 5/1987 | Hollenberg et al. | 424/71 |
| 4,668,508 | 5/1987 | Grollier et al. | 424/70 |
| 4,690,818 | 9/1987 | Puchalski, Jr. et al. | 424/70 |

FOREIGN PATENT DOCUMENTS

| | | |
|---|---|---|
| 0005807 | 12/1979 | European Pat. Off. . |
| 0102736 | 3/1984 | European Pat. Off. . |
| 1149700 | 6/1963 | Fed. Rep. of Germany . |
| 2824025 | 12/1979 | Fed. Rep. of Germany . |

OTHER PUBLICATIONS

Driscoll, William R., "Panthenol in Hair Products," Drug & Cosmetic Ind., Jun., 1975, pp. 42–45 & 149–153.

*Primary Examiner*—Ellis P. Robinson
*Assistant Examiner*—Susan S. Rucker
*Attorney, Agent, or Firm*—Ernest G. Szoke; Wayne C. Jaeschke; Norvell E. Wisdom, Jr.

[57] ABSTRACT

A composition for the regeneration of hair split-ends in an aqueous or aqueous/alcoholic solution or emulsion containing panthenol, at least one mono- or di-saccharide, and optionally polyvinylpyrrolidone and/or a triol; as well as a method for using such composition.

27 Claims, No Drawings

HAIR SPLIT-END REGENERATION COMPOSITION

BACKGROUND OF THE INVENTION

1. Field of the Invention

This invention relates to hair treatment preparations containing a combination of active substances for caring for and revitalizing mistreated hair, more especially for regenerating hair damaged by split ends.

2. Statement of Related Art

Split ends are a phenomenon which is manifested in the hair shaft becoming porous and in splitting of the hair at the ends. Split ends are caused, among other reasons, by severe mechanical stressing of the hair, for example by frequent brushing, backcombing or combing against a high combing resistance. High combing resistance in dry hair can be caused by damage to the hair surface, static charging or tackiness due to remains of hair sprays. The risk of split ends is also increased by weakening of the hair structure which can be caused by frequent or careless use of chemical treatments, for example in permanent waving or dyeing.

Accordingly, there has been no shortage of attempts to regenerate hair damaged by split ends by treatment with suitable preparations, i.e. to halt the further progress of splitting and to restore the damaged hair to a healthy appearance.

Panthenol (2,4-dihydroxy-N-(3-hydroxypropyl)3,3-dimethylbutyramide) is a known constituent of hair conditioning preparations (cf. Drug & Cosmetic Ind., June 1975, 42–45, 149–153).

Reducing sugars have also been described as a structure-improving additive for hair treatment preparations (for example in published German patent application No. 28 24 025).

However, known preparations only show a significant effect when they remain on the hair after application, as is the case with hair setting preparations or hair lotions. By contrast, it has not previously been possible to obtain a satisfactory hair regenerating effect from rinsable hair treatment preparations such as hair treatments, hair rinses or even shampoos because the hair contact time of products such as these is relatively short.

DESCRIPTION OF THE INVENTION

Other than in the operating examples, or where otherwise indicated, all numbers expressing quantities of ingredients or reaction conditions used herein are to be understood as modified in all instances by the term "about".

It has now been found the hair regenerating effect can be enhanced by a combination of panthenol and a mono- or disaccharide so considerably that a high "healing rate" can be observed in the case of badly split hair, even after a very short contact time.

Accordingly the present invention affords hair treatment compositions in the form of aqueous or aqueous/alcoholic solutions or emulsions, which contain as essential ingredients:

(A) panthenol; and
(B) at least one mono- or di-saccharide;
the ingredients (A) and (B) being together present minimally in a hair split-end regenerative effective amount.

Optionally, but preferably, the inventive hair treatment compositions may also contain:
(C) at least one polyvinyl pyrrolidone polymer which, if present, is in a hair split-end regenerative enhancing effective amount; and/or
(D) at least one triol of the formula:

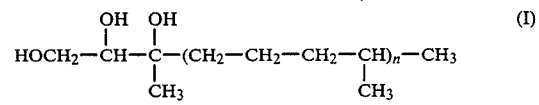

wherein n is an integer from 1 to 3; which if present, is in a hair split-end regenerative enhancing effective amount.

All of the above ingredients are in an aqueous or aqueous/alcoholic, solution or emulsion carrier present q.s. to 100%.

More specific amounts of the above ingredients, in % by weight based upon the total composition, are as follows:

| Ingredient | wt % which may be present | | | |
|---|---|---|---|---|
| | broad ranges | preferred ranges | more preferred ranges | most preferred ranges |
| (A) | 0.1–8.0 | 0.1–8.0 | 0.2–6.0 | 4.0–6.0 |
| (B) | 0.1–8.0 | 0.1–8.0 | 0.5–6.0 | 1.0–6.0 |
| (C) | 0–4.0 | 0.1–4.0 | 0.5–3.0 | 1.5–2.5 |
| (D) | 0–1.0 | 0.01–1.0 | 0.1–1.0 | 0.1–0.5 |

Ingredient (A)—the panthenol may be present both in the D-form and as racemate (D,L-form). However, it has been found that D-panthenol shows greater activity and is therefore preferably used.

ingredient (B)—the mono- or disaccharides are any aldoses and ketoses, or their mixtures, more especially the pentoses (5 C-atoms) and hexoses (6 C-atoms), and also the disaccharides derived from pentoses and hexoses. Suitable monosaccharides include glucose, mannose, galactose, ribose, arabinose, xylose, fructose and sorbose, while suitable disaccharides include sucrose (cane sugar), lactose (milk sugar), maltose (maltsugar) and cellobiose. Also suitable are naturally occurring or technical mixtures in which the mono- and disaccharides mentioned are predominant, for example honey, sugar syrup, invert sugar solutions. Glucose is preferably used, being suitable both in the dextro- or laevo-configuration or as a racemate.

It has also been found that the effectiveness of the combination of panthenol and the mono- or disaccharide may be further enhanced if the hair treatment preparations according to the invention additionally contain ingredients (C) and/or (D) as defined above.

Ingredient (C)—polyvinyl pyrrolidone (PVP) has long been known as a film-forming constituent of hair care preparations. The commercial products have a weight average molecular weight of 10,000 to 360,000 (K-value 15 to 100), are readily soluble in water and, within the average molecular weight range indicated above, are almost all equally suitable for carrying out the invention. A PVP of weight average MW of 30,000 to 50,000 is most preferred, especially 40,000.

Ingredient (D)—triols corresponding to general formula I are known from published German patent application No. 1 149 700. Among the compounds known from this publication, 3,7,11,15-tetramethyl-1,2,3-trihydroxy hexadecane (also known as "dihydro-2,3-dihydroxyphytol" or "phytantriol") is the most important in terms of practical application so that it is particularly preferred for carrying out the invention.

The effectiveness of the combination of panthenol and monoor disaccharide in healing split ends can be doubled by the addition of (C) polyvinyl pyrrolidone. Surprisingly, by contrast, the addition of PVP to d-panthenol alone (without the addition of a mono- or disaccharide) has no effect. The already very good effect of the combination of panthenol and mono- or disaccharide can also be doubled again by the addition of (D) triol especially "phytantriol".

The hair treatment preparations according to the invention may be in the form of aqueous or aqueous/alcoholic, solutions or emulsions. In the most simple case, it is sufficient to dissolve the claimed compulsory components in water or aqueous alcohol as carrier. However, any known hair care preparations in their typical compositions are useful as carriers for the combination of active substances according to the invention. It is possible to use not only hair care preparations which remain on the hair after application, such as hair lotions, hair setting preparations, and pomades, but also those which are rinsed out after treatment of the hair, such as shampoos, rinsing and conditioning lotions and even dyes and permanent wave setting lotions.

In one particularly preferred embodiment, the invention affords hair rinses of the type used, after shampooing, to condition the hair and to reduce the static chargeability of the hair. Hair rinses such as these contain water soluble, surface-active quaternary ammonium, pyridinium or imidazolinium compounds as antistatic agents.

In another preferred embodiment, therefore, the invention relates to hair-treatment preparations whose carriers additionally contain from 0.1 to 5% by weight of such a water soluble, surface-active quaternary ammonium, pyridinium or imidazolinium compound. Besides a water solubilizing quaternary ammonium, pyridinium or imidazolinium moiety, these compounds contain a lipophilic, linear $C_{8-22}$ alkyl or 2-hydroxyalkyl. Examples of such compounds are cetyl pyridinium chloride, 2-alkyl($C_{15}$)-1-(2'-hydroxyethyl)-1-methyl imidazolinium methosulfate and 2-undecyl-1-(2-hydroxyethyl)-1-methyl imidazolinium chloride.

Among the numerous quaternary ammonium compounds, particular significance is attributed to compounds of the formula:

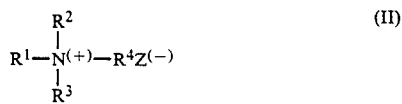

(II)

wherein: $R^1$ is a $C_{8-22}$-alkyl, $C_{8-22}$-2-hydroxyalky, or $R^5CONH(CH_2)_x$—, where $R^5$ is $C_{7-21}$ alkyl and x is a number from 2 to 4; $R^2$ and $R^3$ individually are $C_{1-4}$ alkyl or —$(C_pH_{2p}O)_y$—H, where p is a number from 2 to 4 and y is a number from 1 to 10; and $R^4$ is benzyl or one of the moieties defined for $R^2$ and $R^3$; and Z(—) is a chloride, bromide, hydrogen sulfate, hydrogen phosphate, methoxysulfate or ethoxysulfate anion.

Particularly suitable quaternary ammonium compounds of this type include cetyl trimethyl ammonium chloride, 2-hydroxycetyl-2-hydroxyethyl dimethyl ammonium chloride, lauryl trimethyl ammonium chloride or behenyl trimethyl ammonium chloride.

Hair rinses according to the invention are preferably in the form of an aqueous dispersion where the carrier further comprises:

1 to 5% by weight cetyl or stearyl alcohol,
0.1 to 5% by weight of a water-soluble, surface-active quaternary ammonium, pyridinium or imidazolinium compound, and
0.1 to 1% by weight of a water-soluble saccharide ether.

Suitable water soluble polysaccharide ethers include methyl cellulose, ethyl cellulose, hydroxyethyl cellulose, hydroxypropyl cellulose, methyl hydroxypropyl cellulose and starch or guar derivatives correspondingly substituted by methyl, hydroxyethyl and/or hydroxypropyl groups.

The hair regenerating effect of the hair treatment compositions according to the invention, i.e. their effectiveness in healing split ends, may be considerably enhanced through the choice of the type and quantity of components used. For example, a particularly strong effect is obtained where the compositions contain (A) 0.2 to 6% by weight D(+) panthenol,
(B) 0.5 to 6% by weight glucose, and
(C) 0.5 to 3% by weight polyvinyl pyrrolidone.

An equally good effect is obtained where the compositions contain (A) 0.2 to 6% by weight D(+) panthenol,
(B) 0.5 to 6% by weight glucose, and
(D) 0.1 to 1% by weight 3,7,11,15-tetramethyl-1,2,3-trihydroxy hexadecane.

In addition to hair rinses, hair shampoos may also serve as carriers for the hair-regenerating combination of active substances according to the invention. Shampoos contain high-foam anionic surfactants, preferably sulfate or sulfonate surfactants. These surfactants contain a lipophilic, preferably linear $C_{10-18}$ alkyl chain, and, on this chain, a water-solubilizing sulfate or sulfonate moiety. They are present as water-soluble alkali, magnesium, ammonium or mono-, di- or tri- ($C_{2-3}$) alkanolammonium salts. Examples of suitable anionic surfactants are fatty alcohol-($C_{12-18}$)-sulfates, $C_{12-18}$ fatty alcohol-(1 to 10)-polyglycol ether sulfates, $C_{12-18}$ fatty acid-monoethanolamide(1 to 6)-polyglycol ether sulfates, sulfosuccinic acid mono- and/or diesters of $C_{8-18}$ fatty alcohols, or of $C_{8-18}$ fatty alcohol-(1 to 10)-polyglycol ethers, alpha-sulfo-$C_{12-18}$-fatty acid methyl esters, secondary $C_{12-18}$ alkane sulfonates, alpha-olefin sulfonates and $C_{8-18}$ alkylglyceryl sulfates.

Other surfactants which may be additionally present in the compositions according to the invention may be ampholytic, zwitterionic, and/or nonionic.

Useful ampholytic surfactants contain, in addition to a $C_{8-18}$ alkyl, a free amino moiety and a —COOH— or —$SO_3H$— moiety in the molecule and are capable of forming inner salts.

Examples of useful ampholytic surfactants include 2-($C_{8-18}$)-alkyl-aminopropionic acid or $C_{8-18}$-alkyl-amino-acetic acid.

In addition to a $C_{8-18}$ alkyl, useful zwitterionic surfactants contain a quaternary ammonium moiety and a —COO(—)— or —$SO_3$(—) moiety in their molecule.

Examples of useful zwitterionic surfactants include N-($C_{8-18}$)-alkyl-dimethyl ammonioglycinate, N-(C8-18)-acyl-aminopropyl dimethyl ammonioglycinate, and 2-($C_{8-18}$)-alkyl-3-carboxymethyl-3-hydroxyethyl imidazoline.

Nonionic surfactants useful include the adducts of from 1 to 30 mols ethylene oxide or propylene oxide with $C_{8-22}$ fatty alcohols, with $C_{12-18}$ fatty acids, with $C_{12-18}$ faty amines, with $C_{8-15}$-alkylphenols, with $C_{12-18}$ fatty acid-monoethanolamides, with $C_{12-18}$ fatty acid mono- and diglycerides and with $C_{12-18}$ fatty acid-sorbitan partial esters. Other suitable nonionic surfactants are sugar fatty acid esters, alkyl glucosides and $C_{8-18}$ alkyloligoglycosides, methyl glucoside fatty acid partial esters, and ethylene oxide adducts thereof, and glycerol ethoxylate fatty acid esters. Finally, tertiary aminoeoxides are also suitable nonionic surfactants.

The hair treatment compositions according to the invention may also contain other conventional components typical of the particular formulation, such as
$C_{12-18}$ fatty acid alkanolamides as thickeners and foam boosters,
salts, including $NaCl$, $Na_2SO_4$, $MgCl_2$, $MgSO_4$, as viscosity regulators and to improve the structurant properties,
water soluble polymers containing cationic moieties, for example cellulose ethers containing quaternary ammonium moieties, as conditioning component,
water soluble anionic polymers, for example water soluble polymers containing carboxylate moieties, to improve the setting properties,
cosmetic wax, fat and oil components, silicone oils (polydimethyl siloxanes)
lower alcohols and glycols, such as ethanol, isopropanol, propylene glycol, as solubilizers,
sebostatic and anti-dandruff agents,
dyes,
perfumes, and/or
preservatives.

As mentioned above, the hair-regenerating combination of active substances may also be introduced into hair dyes or permanent-wave setting preparations. These preparations, may contain all the constituents typical of such preparations, no incompatibility having been observed.

The following Examples are intended to illustrate the invention without limiting it in any way.

EXAMPLES

Testing of the Hair-Regenerating Effect

Hair rinses were prepared from the constituents listed in Table 1. The aqueous dispersions according to Examples 1-6 were prepared as follows:

Cetyl/stearyl alcohol (50:50) and glycerol mono-/di-stearate/palmitate were heated together to 80° C. and mixed in molten form. The solution of the cetyl trimethyl ammonium chloride in the water was heated to 80° C. and added with stirring to the melt. The emulsion formed was stirred in the absence of heat. After cooling to around 40° C., the panthenol and glucose and, optionally as indicated the polyvinyl pyrrolidone and phytantriol, were added. Finally, 200 g of a solution of 3% by weight methyl hydroxypropyl cellulose in water were added and the dispersion slowly stirred until it had cooled to 25° C.

In the production of the preparation according to Example 7, cetyl trimethyl ammonium chloride, d-panthenol, glucose and polyvinyl pyrrolidone were dissolved in the water at 30° C.

The hair-regenerating effect was tested on a sample of 100 hairs all of which had been split by mechanical and electrostatic pretreatment. The hairs were treated for 10 minutes with the undiluted preparations of Examples 1 to 7. The hairs were then rinsed with tap water, dried and combed. The visually discernible split ends were then determined by counting, a lower number being preferable.

In every case, it was found that the hairs had been regenerated, i.e. the split-ends had been partially repaired.

The test described above was additionally carried out with the composition of Example 2 without subsequent rinsing of the hair treatment composition from the hair. In this case, the treatment composition was removed solely mechanically (by squeezing) from the hair. After drying and combing, the split rate was only 10%. This shows that the advantages of the hair treatment preparations according to the invention are particularly in evidence with rinsable preparations.

The general method for regeneration of hair split-ends according to this invention comprises applying the inventive composition to hair having split-ends and permitting it to remain on the hair for at least a split-end regenerative effective length of time. The inventive composition may then be allowed to remain on the hair indefinitely, in which instance it may be in the form of a pomade, setting gel, mousse, or the like. Alternatively, the inventive composition may be removed from the hair, typically by rinsing with water, after it has remained in contact minimally for a split-end regenerative effective amount of time. The usual contact time is 5 to 30 minutes, preferably 5 to 15 minutes, more preferably 10 minutes

TABLE

| | Example | | | | | | |
|---|---|---|---|---|---|---|---|
| | comparison | | | invention | | | |
| Ingredient | 1 | 2 | 3 | 4 | 5 | 6 | 7 |
| Cetostearyl alcohol | 4 | 4 | 4 | 4 | 4 | 4 | — |
| GMS(1) | 3 | 3 | 3 | 3 | 3 | 3 | — |
| CTAC(2) | 2 | 2 | 2 | 2 | 2 | 2 | 1 |
| MHPC (3% solution)(3) | 20 | 20 | 20 | 20 | 20 | 20 | — |
| Water | 70 | 66 | 64 | 61 | 59 | 63.8 | 90 |
| (A) d-Panthenol | 1 | 5 | 5 | 5 | 5 | 5 | 5 |
| (B) Glucose monohydrate | — | — | — | 5 | 5 | 2 | 2 |
| (C) PVP(4) | — | — | 2 | — | 2 | — | 2 |
| (D) Phytantriol | — | — | — | — | — | 0.2 | — |
| percentage of split-ends remaining | 50 | 35 | 50 | 20 | 10 | 10 | 20 |

(1)GMS: glycerol mono-/di-stearate/palmitate
(2)CTAC: cetyl trimethyl ammonium chloride (quaternary surfactant)
(3)MHPC: methyl hydroxypropyl cellulose, average molecular weight approx. 3000, 3% solution in water. (water soluble polysaccharide ether)
(4)PVP: polyvinyl pyrrolidone (weight average MW: approx. 40,000 ("Luviskol" K30, a product of BASF AG, Ludwigshafen, Germany)

Analysis of Testing Results

Comparison Examples 1–3 show the effect of the compositions containing only panthenol (Examples 1 and 2) and only both panthenol and PVP (Example 3). Invention example 4 demonstrates the unexpectedly increased effect of the combination of d-panthenol and glucose. Invention examples 5 and 6 show that the effect is still further enhanced by either PVP or phytantriol. Invention Example 7 shows that the effect is also obtained with a clear, aqueous (i.e. non-alcoholic) preparation containing PVP.

We claim:

1. A composition for the regeneration of hair split-ends in an aqueous or aqueous/alcoholic, solution or emulsion carrier, consisting essentially of:
   (A) panthenol; and
   (B) at least one mono- or di-saccharide; the ingredients (A) and (B) being together present minimally in a hair split-end regenerative effective amount; and optionally also consisting essentially of:

(C) at least one polyvinyl pyrrolidone polymer; and/or (D) at least one triol of the formula:

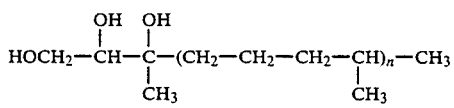

wherein n is an integer from 1 to 3;
the ingredients (C) and (D), if present, individually being in a hair split-end regenerative enhancing effective amount.

2. The composition of claim 1 wherein ingredient:
(A) is present in about 0.1 to 8.0 wt %;
(B) is present in about 0.1 to 8.0 wt %;
(C) may be present in 0 to about 4.0 wt %; and
(D) may be present in 0 to about 1.0 wt %;
all percentages being based upon the total weight of the composition.

3. The composition of claim 1 wherein ingredient:
(A) is present in about 0.1 to 8.0 wt %;
(B) is present in about 0.1 to 8.0 wt %;
(C) is present in about 0.1 to 4.0 wt %; and
(D) is present in about 0.01 to 1.0 wt %;
all percentages being based upon the total weight of the composition.

4. The composition of claim 1 wherein ingredient:
(A) is present in about 0.2 to 6.0 wt %;
(B) is present in about 0.5 to 6.0 wt %;
(C) is present in about 0.5 to 3.0 wt %; and
(D) is present in about 0.1 to 1.0 wt %;
all percentages being based upon the total weight of the composition.

5. The composition of claim 1 wherein ingredient:
(A) is present in about 4.0 to 6.0 wt %;
(B) is present in about 1.0 to 6.0 wt %;
(C) is present in about 1.5 to 2.5 wt %; and
(D) is present in about 0.1 to 0.5 wt %;
all percentages being based upon the total weight of the composition.

6. The composition of claim 1 wherein ingredient:
(A) is present in about 5.0 wt %;
(B) is present in about 2.0 to 5.0 wt %;
(C) is present in about 2 wt %; and
(D) is present in about 0.2 wt %;
all percentages being based upon the total weight of the composition.

7. The composition of claim 1 wherein (A) is dextro-panthenol.

8. The composition of claim 1 wherein (B) is at least one aldose, ketose, or mixture thereof.

9. The composition of claim 1 wherein (B) is at least one pentose, hexose, or disaccharide derived from a pentose or hexose.

10. The composition of claim 1 wherein (B) is at least one of: glucose, mannose, galatose, ribose, arabinose, xylose, fructose, sorbose, sucrose, lactose, maltose, or cellobiose.

11. The composition of claim 1 wherein (B) is glucose.

12. The composition of claim 1 wherein (C) is present.

13. The composition of claim 11 wherein (C) is present and is at least one water soluble polyvinyl pyrrolidone polymer having a weight average molecular weight of about 10,000 to 360,000.

14. The composition of claim 1 wherein (D) is present and n is 1.

15. The composition of claim 1 wherein (D) is present and n is 2.

16. The composition of claim 1 wherein (D) is present and n is 3.

17. The composition of claim 1 wherein both (C) and (D) is present.

18. The composition of claim 6 wherein (B) is at least one pentose, hexose, or disaccharide derived from a pentose or hexose.

19. The composition of claim 17 wherein (C) is present.

20. The composition of claim 17 wherein (D) is present.

21. The composition of claim 18 wherein (D) is present.

22. The composition of claim 1 wherein:
(A) is dextro-panthenol and is present in about 0.2 to 6.0 wt %;
(B) is glucose and is present in about 0.5 to 6.0 wt %; and
(C) is present in about 0.5 to 3.0 wt %;
all percentages being based upon the total weight of the composition.

23. The composition of claim 1 wherein:
(A) is dextro-panthenol and is present in about 0.2 to 6.0 wt %;
(B) is glucose and is present in about 0.5 to 6.0 wt %; and
(D) is 3,7,11,15-tetramethyl-1,2,3-trihydroxyhexadecane and is present in about 0.1 to 1.0 wt %;
all percentages being based upon the total weight of the composition.

24. The composition of claim 1 wherein said carrier further comprises at least one water-soluble quaternary ammonium, pyridinium, or imidazolinium compound present in a surfactant-effective amount.

25. The composition of claim 1 wherein said carrier further comprises:
about 1.0 to 5.0 wt % of cetyl or stearyl alcohol or their mixture;
about 0.1 to 5.0 wt % of a water soluble quaternary ammonium, pyridinium, or imidazolinium compound surfactant; and
about 0.1 to 1.0 wt % of a water soluble polysaccharide ether.

26. A method for the regeneration of hair split-ends comprising applying to said hair a split-end regenerative effective amount of the composition of claim 1.

27. The method of claim 25 with the further step of removing said composition from said hair after contact therewith for a split-end regenerative effective length of time.

* * * * *